(12) United States Patent
Fuladi

(10) Patent No.: US 12,295,984 B2
(45) Date of Patent: *May 13, 2025

(54) TOPICAL COMPOSITION FOR PAIN RELIEF

(71) Applicant: Bob Fuladi, Santa Barbara, CA (US)

(72) Inventor: Bob Fuladi, Santa Barbara, CA (US)

( * ) Notice: Subject to any disclaimer, the term of this patent is extended or adjusted under 35 U.S.C. 154(b) by 979 days.

This patent is subject to a terminal disclaimer.

(21) Appl. No.: 17/370,047

(22) Filed: Jul. 8, 2021

(65) Prior Publication Data

US 2021/0330733 A1 Oct. 28, 2021

Related U.S. Application Data

(63) Continuation-in-part of application No. 16/708,608, filed on Dec. 10, 2019, now Pat. No. 11,058,651, which is a continuation-in-part of application No. 16/009,067, filed on Jun. 14, 2018, now Pat. No. 10,517,821.

(51) Int. Cl.

| | |
|---|---|
| *A61K 36/9066* | (2006.01) |
| *A61K 9/00* | (2006.01) |
| *A61K 9/06* | (2006.01) |
| *A61K 31/10* | (2006.01) |
| *A61K 31/125* | (2006.01) |
| *A61K 31/167* | (2006.01) |
| *A61K 31/216* | (2006.01) |
| *A61K 36/28* | (2006.01) |
| *A61K 47/10* | (2017.01) |
| *A61K 47/12* | (2006.01) |
| *A61K 47/14* | (2017.01) |
| *A61K 47/26* | (2006.01) |
| *A61K 47/44* | (2017.01) |

(52) U.S. Cl.
CPC ........ *A61K 36/9066* (2013.01); *A61K 9/0014* (2013.01); *A61K 9/06* (2013.01); *A61K 31/10* (2013.01); *A61K 31/125* (2013.01); *A61K 31/167* (2013.01); *A61K 31/216* (2013.01); *A61K 36/28* (2013.01); *A61K 47/10* (2013.01); *A61K 47/12* (2013.01); *A61K 47/14* (2013.01); *A61K 47/26* (2013.01); *A61K 47/44* (2013.01)

(58) Field of Classification Search
None
See application file for complete search history.

(56) References Cited

U.S. PATENT DOCUMENTS

| | | |
|---|---|---|
| 6,579,543 B1 | 6/2003 | McClung |
| 8,337,869 B2 | 12/2012 | Gross |
| 9,095,563 B2 | 8/2015 | Sekura et al. |
| 2003/0180347 A1 | 9/2003 | Young et al. |
| 2006/0194759 A1 | 8/2006 | Eidelson |

FOREIGN PATENT DOCUMENTS

| | | | |
|---|---|---|---|
| CN | 101780239 A | * | 7/2010 |
| JP | 2010070501 A | | 4/2010 |

* cited by examiner

*Primary Examiner* — Michael V Meller
(74) *Attorney, Agent, or Firm* — Paul D. Chancellor; Ocean Law

(57) ABSTRACT

A topical composition for nociceptive and neuropathic pain relief comprising one or more of menthol, camphor, methyl sulfonyl methane, lidocaine, *arnica montana*, *harpagophytum* tincture, Emu oil, maqui powder, *piper nigrum,* turmeric oil and in some embodiments acetyl or methyl salicylate or capsaicin with *cannabis sativa*.

1 Claim, 3 Drawing Sheets

FIG. 1

| Item | Ingredient | Weight Percent (%) |
|---|---|---|
| 1 | Methyl Salicylate | 15 |
| 2 | Menthol | 8 |
| 3 | Camphor | 3 |
| 4 | MSM | 5 |
| 5 | Lidocaine | 2 |
| 6 | Arnica Montana | 5 |
| 7 | Devil Extract (Harpagophytum tincture) | |
| 8 | Emu Oil | |
| 9 | Maqui Powder | |
| 10 | Curcumin extract or Curcuma Longa (Tumeric) oil or curcumin aromatica or curcumin aromatica non-staining | |

| Item | Ingredient | Weight Percent (%) |
|---|---|---|
| 1 | Capsaicin extract | 0.28 |
| 2 | Cannabis Sativa (Hemp) oil | |
| 3 | Menthol | 8 |
| 4 | Camphor | 3 |
| 5 | MSM | |
| 6 | Lidocaine | 2 |
| 7 | Arnica Montana | 5 |
| 8 | Devil Extract (Harpagophytum tincture) | |
| 9 | Emu Oil | |
| 10 | Maqui Powder | |
| 11 | Curcumin extract or Curcuma Longa (Tumeric) oil or curcumin aromatica or curcumin aromatica non-staining | |

FIG. 3

| Ingredient | Purpose |
|---|---|
| Aloe Vera | anti-inflammatory/skin permeation and repair |
| Arnica Montana (Flower extract) obtained from 5% w/w of raw material* | analgesic |
| Bergamot oil | analgesic/relaxant/improved circulation |
| Camphor | analgesic/anti-itch/counterirritant |
| Cannabis Sativa (Hemp) oil | analgesic/anti-inflammatory |
| Capsaicin extract obtained from 0.75% raw material | analgesic |
| Curcumin extract or Curcuma Longa (Tumeric) oil or curcumin aromatica or curcumin aromatica non-staining | anti-inflammatory/antioxidant/analgesic |
| Emu Oil | anti-inflammatory/skin moisturizer |
| Ginger extract obtained from 1%w/w of raw Ginger* | anti-inflammatory/antioxidant |
| Harpagophytum tincture (Devil extract) obtained from 2.5% w/w of raw material* | analgesic/anti-inflammatory |
| Lidocaine | local anesthesia |
| Maqui powder* | potent antioxidant |
| Menthol | local anesthetic, analgesic |
| Methyl Salicylate | counterirritant/analgesic |
| MSM (Methyl sulfonyl methane) | anti-inflammatory, skin permeation and repair |
| Piper nigrum (Black pepper) oil | enhancement of curcumin bioavailability, anti-inflammatory |

300

TOPICAL COMPOSITION FOR PAIN RELIEF

PRIORITY CLAIM

This application is a continuation-in-part of U.S. patent application Ser. No. 16/708,608 filed Dec. 10, 2019 and entitled Topical Composition for Pain Relief which is a continuation-in-part of U.S. patent application Ser. No. 16/009,067 filed Jun. 14, 2018, now U.S. Pat. No. 10,517,821, and entitled Topical Composition for Pain Relief.

BACKGROUND OF THE INVENTION

Many people suffer from pains including musculoskeletal conditions such as soft tissue trauma and arthritis. Some bear the pain associated with those conditions for prolonged periods. Treatment of musculoskeletal pain using traditional analgesics and anti-inflammatory drugs and known combinations of traditional analgesics anti-inflammatory drugs is not always effective.

Field of Invention

This invention relates to the medicinal/chemical arts and to the treatment of nociceptive and neuropathic pain in humans.

Discussion of the Related Art

Medications for the relief of pain may include analgesics and anti-inflammatories. However, compositions that include these ingredients along with local anesthetics and/or counterirritants are not well known.

SUMMARY OF THE INVENTION

The present invention provides a composition or topical cream useful for treating nociceptive and neuropathic pain in humans.

In an embodiment, a composition includes by weight percent about 10% of counterirritant/analgesic methyl salicylate, 4% of anesthetic/analgesic, 5% of skin permeator/anti-inflammatory, 2% of analgesic/anti-itch/counterirritant, 5% of analgesic, 2.6% of analgesic/anti-inflammatory, 4% of anesthetic, 1% of antioxidant. In various embodiments, the ingredients of this composition are varied in a range of plus or minus 50%; for example, the anesthetic/analgesic is varied from 4% to 12%. In various embodiments, the ingredients of this composition are varied in a range of plus or minus 40%, in a range of plus or minus 30%, in a range of plus or minus 20%, in a range of plus or minus 10%, in a range of plus or minus 5%.

In an embodiment, a composition includes by weight percent about 8% of anesthetic/analgesic menthol, 5% of anti-inflammatory/skin permeator, 5% of analgesic, 3% of analgesic/anti-itch/counterirritant, 2.5% of analgesic/anti-inflammatory, 4% of anesthetic, 0.25% of analgesic. In various embodiments, the ingredients of this composition are varied in a range of plus or minus 50%; for example, the anesthetic/analgesic ingredient is varied from 4% to 12%. In various embodiments, the ingredients of this composition are varied in a range of plus or minus 40%, in a range of plus or minus 30%, in a range of plus or minus 20%, in a range of plus or minus 10%, in a range of plus or minus 5%.

In an embodiment, a composition includes therapeutically effective amounts of acetyl or methyl salicylate, methyl sulfonyl methane, *arnica montana,* camphor, menthol, *harpagophytum* tincture, lidocaine, and maqui. The composition may further include any of ginger extract, emu oil, aloe vera, *piper nigrum,* non-staining *curcuma,* lavender oil or mint oil, jagged ice or clear white color formula, stearic acid, cetyl alcohol, isopropyl palmitate, sodium Benzoate, sorbitan monostearate, ethylhexylglycerin, sorbitol solution, polysorbate 60, and purified water.

In an embodiment, a composition includes therapeutically effective amounts of acetyl salicylate, methyl sulfonyl methane, lidocaine, *arnica montana,* ginger extract, *piper nigrum,* non-staining clear curcumin extract, *harpagophytum* tincture, menthol, camphor, maqui powder, emu oil, and aloe vera. The composition may further include any of mint oil or lavender oil, jagged ice color or clear white color formula, stearic acid, cetyl alcohol, isopropyl palmitate, sodium benzoate, sorbitan monostearate, ethylhexylglycerin, sorbitol solution, polysorbate 60, and purified water.

In an embodiment, a composition includes therapeutically effective amounts of capsaicin extract, methyl sulfonyl methane, lidocaine, *arnica montana,* ginger extract, *harpagophytum* tincture, menthol, camphor, glucosamine, emu oil, aloe vera, *piper nigrum* oil, *curcuma aromatica* or *zedoaria* oil or non-staining clear curcumin extract, and *cannabis sativa* oil. The composition may further include any of lavender oil or mint oil, natural cream color or clear white color formula, stearic acid, cetyl alcohol, isopropyl palmitate, sodium benzoate, sorbitan monostearate, ethylhexylglycerin, sorbitol solution, polysorbate 60, Carbopol 940, and purified water.

BRIEF DESCRIPTION OF THE DRAWINGS

The present invention is described with reference to the accompanying figures. These figures, incorporated herein and forming part of the specification, illustrate the present invention and, together with the description, further explain the principles of the invention and to enable a person skilled in the relevant art to make and use the invention.

FIG. 1 shows an embodiment of the invention wherein acetyl or methyl salicylate is a main ingredient.

FIG. 2 shows an embodiment of the invention where capsaicin and hemp oil are ingredients used in place of acetyl or methyl salicylate.

FIG. 3 shows the purpose of the ingredients used in the invention.

DETAILED DESCRIPTION OF THE PREFERRED EMBODIMENTS

The disclosure provided in the following pages describes examples of some embodiments of the invention. The designs, figures, and descriptions are non-limiting examples of certain embodiments of the invention. For example, other embodiments of the disclosed device may or may not include the features described herein. Moreover, disclosed advantages and benefits may apply to only certain embodiments of the invention and should not be used to limit the disclosed inventions.

In an embodiment, the invention comprises the ingredients shown in Table 1 below.

TABLE 1

Topical Composition for Pain Relief
Ingredients In A First Embodiment

| Item | Ingredients | Supplier (Lot number) + other information | % W/W | ASA-90 gm batch (gm) |
|---|---|---|---|---|
| 1 | Acetyl or Methyl Salicylate | Spectrum | 10.0 | 9.0 |
| 2 | MSM (Methyl sulfonyl methane) | Source Naturals (SN1535 REVK151) | 5.00 | 4.5 |
| 3 | Lidocaine | Spectrum USP (IEC0028) | 4.0 | 3.6 |
| 4 | Arnica Montana (Flower extract) obtained from 5% w/w of raw material | TerraVita (512592) | 5.0 | 4.5 |
| 5 | Ginger extract obtained from 1% w/w of raw Ginger | Starwest Botanical (68499) | 0.6 | 0.5 |
| 6 | Harpagophytum tincture (Devil's claw extract) | Varies (TBD) | 2.6 | 2.3 |
| 7 | Menthol | Spectrum (1EE0771) | 4.0 | 3.6 |
| 8 | Camphor | Spectrum (2EC0027) | 2.0 | 1.8 |
| 9 | Maqui powder extract | South Life (MFDP2016-08) | 1.0 | 0.9 |
| 10 | Emu Oil | Varies (TBD) | 1.0 | 0.9 |
| 11 | Aloe Vera | Varies (TBD) | 1.0 | 0.9 |
| 12 | Piper nigrum (Black pepper) oil | Varies (TBD) | 0.1 | 0.1 |
| 13 | Curcuma Aromatica or Curcuma Zedoaria (Clear non-staining turmeric) | Varies (TBD) | 1.0 | 0.9 |
| 14 | Mint oil and Lavender oil | Varies (TBD) | 0.4 (0.2, 0.2) | 0.4 (0.2, 0.2) |
| 15 | Jagged ice (Dae8f1) or white color formula | Varies (TBD) | 0.25 | 0.2 |
| 16 | Cream Base* (Vanishing Cream formula) | Varies (TBD) | 22.2 | 20.0 |
| 17 | Cream Base (See Table 2) | | 39.85 | 35.9 |
| | Totals | | 100 | 90 |

The cream base referred to in Table 1 is shown in Table 2 below.

TABLE 2

First Cream Base

| Item | Ingredients | Supplier (Lot number) + other information | % W/W | ASA-90 gm batch (gm) |
|---|---|---|---|---|
| 1 | Stearic acid | Spectrum NF (2FF0167) | 15.53 | 14.0 |
| 2 | Cetyl Alcohol | USB (36653-82-4) | 1.00 | 0.9 |
| 3 | Isopropyl Palmitate | Spectrum NF (2F10111) | 1.00 | 0.9 |
| 4 | Sodium Benzoate | Varies (TBD) | 0.33 | 0.3 |
| 5 | Sorbitan Monostearate | Spectrum NF (2FG0337) | 5.00 | 4.5 |
| 6 | Ethylhexylglycerin | Varies (TBD) | 0.33 | 0.3 |
| 7 | Sorbitol Solution (70%) | Spectrum USP (1GC1050) | 3.00 | 2.7 |
| 8 | Polysorbate 60 | Spectrum NF (L-15031-AP) | 5.00 | 4.5 |
| 9 | Carbopol 940 | Lutriol | 0.33 | 0.3 |
| 10 | Purified water q.s. | In House | 8.33 | 7.5 |
| | BATCH TOTAL | | 100% | 90 GMs |

Manufacturing Procedure

In a first step, weigh specified amounts of MSM, emu oil, maqui powder extract, ginger extract, *arnica montana* flower extract, devils claw extract, Aloe vera, ethylhexylglycerin, sorbitol solution, polysorbate 60, Carbopol 940 and purified water in a suitable glass container and heat to 80±5° C. on a heated water bath and stir the mixture to disperse the mixture completely.

In a second step, weight and mix specified amounts of methyl salicylate, lidocaine, stearic acid, cetyl alcohol, isopropyl palmitate, sodium benzoate, *piper nigrum* (black pepper) oil, *curcuma aromatica* or *zedoaria* (turmeric) oil, and sorbitan monostearate separately in a suitable glass container and heat to 80±5° C. on a heated water bath. Stir the dispersion to mix all components.

In a third step, mix the components of step-II with the components of step-I at 80±5° C. under continuous homogenization for 10-15 minutes.

In a fourth step, remove the mixture from the heated water bath, add specified amount of menthol, camphor, jagged ice Dae8f1 or white color formula and flavoring agent (lavender and mint oil) and stir continuously to disperse them uniformly.

In a fifth step, add the cream base.

In a sixth step, when the temperature of the composition is just above solidification, the formulation is poured into suitable well labeled aluminum tubes, plastic jars or containers. The final product is cooled down to room temperature, capped and stored at room temperature.

In an embodiment, the invention comprises the ingredients shown in Table 3 below.

TABLE 3

Topical Composition for Pain Relief
Ingredients In A Second Embodiment

| Item | Ingredients | Supplier (Lot number) + other information | % W/W | For 90 gm batch non-ASA (gm) |
|---|---|---|---|---|
| 1 | Capsaicin extract obtained from 0.75% raw material | Starwest Botanical (70519) | 0.25 | 0.2 |
| 2 | MSM (Methyl sulfonyl methane) | Source Naturals (SN1535 REVK151) | 5 | 4.5 |
| 3 | Lidocaine | Spectrum USP (IEC0028) | 4.0 | 3.6 |
| 4 | Arnica Montana (Flower extract) obtained from 5% w/w of raw material | TerraVita (512592) | 5.0 | 4.5 |
| 5 | Ginger extract obtained from 1% w/w of raw Ginger | Starwest Botanical (68499) | 0.6 | 0.5 |

TABLE 3-continued

Topical Composition for Pain Relief
Ingredients In A Second Embodiment

| Item | Ingredients | Supplier (Lot number) + other information | % W/W | For 90 gm batch non-ASA (gm) |
|---|---|---|---|---|
| 6 | Harpagophytum tincture (Devil's claw extract) | varies (TBD) | 2.5 | 2.3 |
| 7 | Menthol | Spectrum (1EE0771) | 8 | 7.2 |
| 8 | Camphor | Spectrum (2EC0027) | 3 | 2.7 |
| 9 | Glucosamine | Varies (TBD) | 0.3 | 0.3 |
| 10 | Emu Oil | Varies (TBD) | 0.3 | 0.3 |
| 11 | Aloe Vera | Varies (TBD) | 1 | 0.9 |
| 12 | Piper nigrum (Black pepper) oil | Varies (TBD) | 0.1 | 0.1 |
| 13 | Curcuma Aromatica or Curcuma Zedoaria (non-staining turmeric extract) | Varies (TBD) | 1.0 | 0.9 |
| 14 | Cannabis Sativa (Hemp) oil | Varies (TBD) | 1.0 | 0.9 |
| 15 | Lavender oil | Varies (TBD) | 0.25 | 0.2 |
| 16 | Cream Color formula | Varies (TBD) | 0.25 | 0.2 |
| 17 | Vanishing Cream formula | Varies (TBD) | 25.0 | 22.5 |
| 18 | Cream Base (See Table 4) | | 42.45 | 38.2 |
| | Totals | | 100 | 90 |

The cream base referred to in Table 3 is shown in Table 4 below.

TABLE 4

Second Cream Base

| Item | Ingredients | Supplier (Lot number) + other information | % W/W | ASA-90 gm batch (gm) |
|---|---|---|---|---|
| 1 | Stearic acid | Spectrum NF (2FF0167) | 15.0 | 13.5 |
| 2 | Cetyl Alcohol | USB (36653-82-4) | 1.00 | 0.9 |
| 3 | Isopropyl Palmitate | Spectrum NF (2F10111) | 1.00 | 0.9 |
| 4 | Sodium Benzoate | Varies (TBD) | 0.35 | 0.3 |
| 5 | Sorbitan Monostearate | Spectrum NF (2FG0337) | 5.00 | 4.5 |
| 6 | Ethylhexylglycerin | Varies (TBD) | 0.35 | 0.3 |
| 7 | Sorbitol Solution (70%) | Spectrum USP (1GC1050) | 3.00 | 2.7 |
| 8 | Polysorbate 60 | Spectrum NF (L-15031-AP) | 5.00 | 4.5 |
| 9 | Carbopol 940 | Lutriol | 0.25 | 0.2 |
| 10 | Purified water q.s. | In House | 11.5 | 10.4 |
| | Cream Base Totals | | 42.45 | 38.2 |

In some embodiments, the methyl salicylate listed in Table 1 is included in the list of ingredients shown in Table 3 with or without the capsaicin extract. The weight percent of this additional ingredient may be 10% with the cream base reduced by a corresponding amount. If the capsaicin extract is excluded, the cream base may be increased by a corresponding amount.

Manufacturing Procedure

In a first step, weigh specified amounts of MSM, emu oil, glucosamine, ginger extract, *Arnica Montana* Flower extract, devils claw extract, aloe vera, ethylhexylglycerin, sorbitol solution, polysorbate 60, Carbopol 940 and purified water in a suitable glass container and heat to 80±5° C. on a heated water bath and stir the mixture to disperse the mixture completely.

In a second step, weight and mix specified amounts of capsaicin extract, lidocaine, stearic acid, cetyl alcohol, isopropyl palmitate, sodium benzoate, *piper nigrum* (black pepper) oil, *curcuma aromatica* or *zedoaria* (turmeric) oil, *cannabis sativa* (hemp) oil and sorbitan monostearate separately in a suitable glass container and heat to 80±5° C. on a heated water bath. Stir the dispersion to mix all components.

In a third step, mix the components of step-II with the components of step-I at 80±5° C. under continuous homogenization for 10-15 minutes.

In a fourth step, remove the mixture from the heated water bath, add specified amount of menthol, camphor, natural cream color formula and flavoring agent (lavender oil) and homogenize continuously to disperse them uniformly.

In a fifth step, add the cream base.

In a sixth step, when the temperature of the composition is just above solidification, the formulation is poured into suitable well labeled aluminum tubes, plastic jars or containers. The final product is cooled down to room temperature, capped and stored at room temperature.

FIG. 1 shows the main ingredients 100 of a topical composition for pain relief used in an embodiment containing methyl salicylate. FIG. 2 shows the main ingredients 200 of a topical composition for pain relief used in an embodiment where hemp oil and capsaicin extract are used in place of methyl salicylate. FIG. 3 shows the purpose 300 of each of the topical composition for pain relief ingredients.

Experimental Results

It has been found that the composition can be used to treat generalized muscle and joint pain and inflammation. For example, the composition can be used: as a topical anti-inflammatory to treat localize inflammation; as a moisturizer and conditioner for the skin as a secondary effect when used for the purpose of reducing pain or inflammation as described above; in conjunction with other systemic anti-inflammatories as in a gouty attack, resulting in significant reduction in pain and inflammation. Localized pain relief is provided for up to 8 to 12 hours.

Recommendations for Use

Pregnancy: Use not recommended in pregnancy. Consult with your Physician prior to use.

Interactions and Precautions: Consult with your Physician if on blood thinners, have kidney, liver or heart disease, and/or suffer from high blood pressure. Use only under the explicit guidance and approval of a physician if any of the above conditions exist. Allergy: Do not use this product if allergic to aspirin or to any of the active or inactive ingredients listed on the package.

Caution: Do not use with alcohol or any other topical medication. Consult a physician or a pharmacist for possible cross-reactions or interactions when taking or using other medications. Long-term use is not recommended. Chronic use beyond 7 days should be done under the supervision/guidance of a physician.

Application

For use, the composition is typically rubbed onto the skin in the areas of pain and/or inflammation, two or three times daily. Apply the cream to a small section of the affected area prior to more generalized use. Immediately stop using the cream and notify your Physician in the event of any allergic or hypersensitivity reaction. If an allergic reaction such as a rash, hives or a more severe reaction occurs, consult a medical professional immediately or call 911 should the reaction appear to be life threatening.

What follows is a random selection of exemplary results. Pain levels are recorded based on a scale of 1-3 low pain, 4-6 moderate pain, and 7-10 severe pain. Inflammation levels are recorded based on a scale of 1 for no reduction in swelling to 10 for a profound reduction in swelling. Patients 1 and 2 were treated with the first embodiment of the topical composition for pain relief. Other patients were treated with the second embodiment of the topical composition for pain relief.

Patient 1: An adult male complained of chronic back pain. A severe pain baseline of 7 was determined before use of the topical composition for pain relief. Inflammatory response was not measured. After use of the cream, a moderate pain level of 4 was determined. No adverse side effects were observed.

Patient 2: An adult male complained of a right ankle bone bruise. A moderate pain baseline of 5 was determined before use of the topical composition for pain relief. After use of the cream, a low pain level of 1 was determined along with an inflammation response of 3. No adverse side effects were observed.

Patient 3: An adult male complained of a wrist sprain. A moderate pain baseline of 6 was determined before use of the topical composition for pain relief. After use of the cream, a low pain level of 1 was determined along with an inflammation response of 3. No adverse side effects were observed.

Patient 4: An adult male complained of Achilles tendonitis. A moderate pain baseline of 5 was determined before use of the topical composition for pain relief. After 3 days of use, applying the cream twice a day, a low pain level of 1 was determined along with an inflammation response of 9. No side effects were observed.

Patient 5: An adult male complained of arthritis following knee surgery and removal of a majority of the medial meniscus. A moderate pain baseline of 4 was determined before the use of the topical composition for pain relief. After three applications of the cream over a two-day period, the discomfort essentially disappeared and a pain level of 1 was determined along with an inflammation response of 5. Side effect was noticeable smell of cream during first hour after application.

While various embodiments of the present invention have been described above, they have been presented by way of example only, and not limitation. It will be apparent to those skilled in the art that various changes in the form and details can be made without departing from the spirit and scope of the invention. As such, the breadth and scope of the present invention should not be limited by the above-described exemplary embodiments, but should be defined only in accordance with the following claims and equivalents thereof.

What is claimed is:

1. A method for treating pain in a human in need thereof consisting essentially of administering to the human in need thereof therapeutically effective amounts of methyl salicylate, methyl sulfonyl methane, *arnica montana*, camphor, *harpagophytum* tincture, lidocaine, *curcuma zedoaria* oil, curcumin aromatica, and maqui to effectively treat the pain in the human in need thereof.

* * * * *